United States Patent [19]

Hatada et al.

[11] 4,265,276

[45] May 5, 1981

[54] PLASTIC TUBE HAVING A CROSSLINKED THIN LAYER ON THE SURFACE

[75] Inventors: Kenji Hatada; H. Kobayashi; Miyoshi Yokura, all of Otsu, Japan

[73] Assignee: Toray Industries, Inc., Tokyo, Japan

[21] Appl. No.: 110,836

[22] Filed: Jan. 10, 1980

Related U.S. Application Data

[63] Continuation of Ser. No. 948,707, Oct. 5, 1978, abandoned.

[30] Foreign Application Priority Data

Oct. 14, 1977 [JP] Japan ............................. 52-122529

[51] Int. Cl.³ ............................................. F16L 9/12
[52] U.S. Cl. ................................ 138/177; 138/118; 128/349 R; 428/36; 428/216; 428/913; 204/165; 264/DIG. 2
[58] Field of Search ............... 138/125, 126, 137, 140, 138/177, 118; 128/348, 349 R, 350 R; 428/36, 215, 216, 212, 213, 336, 910, 913; 204/165; 264/DIG. 42

[56] References Cited

U.S. PATENT DOCUMENTS

| | | | |
|---|---|---|---|
| 2,317,987 | 5/1943 | Flynn | 138/118 |
| 2,645,249 | 7/1953 | Davis et al. | 138/137 X |
| 3,115,164 | 12/1963 | Vanderbilt | 138/125 |
| 3,384,089 | 5/1968 | Shriner | 138/137 X |
| 3,687,832 | 8/1972 | Fydelor et al. | 204/165 |
| 3,741,253 | 6/1973 | Brax et al. | 138/137 |
| 3,749,134 | 7/1973 | Slingluff et al. | 138/118 X |
| 4,044,187 | 8/1977 | Kremkau | 138/118 X |
| 4,089,360 | 5/1978 | Bohm | 138/126 X |

FOREIGN PATENT DOCUMENTS 1161259  8/1969  United Kingdom .

Primary Examiner—James E. Bryant, III
Attorney, Agent, or Firm—Miller & Prestia

[57] ABSTRACT

Polyvinyl chloride tube having a crosslinked thin layer of about 0.1 to about 1 micron in thickness at least on its inner surface, thereby substantially reducing the migration and volatilization of plasticizers and other additives from the polymeric materials into the fluid in said tube. The tube of this invention is especially useful for medical use.

4 Claims, 2 Drawing Figures

PLASTIC TUBE HAVING A CROSSLINKED THIN LAYER ON THE SURFACE

This is a continuation of application Ser. No. 948,707, filed Oct. 5, 1978, now abandoned.

SUMMARY OF THE INVENTION

The present invention relates to an improvement in tubing by reducing the migration and volatization of plasticizers and other additives from the polymeric materials of the tube into fluids flowing therein. Many kinds of plastic tubes are used for conduit tubing of fluids, such as blood for blood transfusion, urine for an artificial kidney and oil of automobiles. In many cases relatively lower molecular weight substances such as additives are blended in the polymeric materials of tubes for the sake of improving their various properties. Additives include, for example, plasticizers, antioxidants and ultraviolet absorbers. These additives easily migrate and volatilize from the bulk of a tube to the fluid flowing therein. This often causes a crucial disadvantage in that tubes become brittle, and fluid is contaminated by the migrated additives. To prevent additives from migration and volatility, the surface barrier is preferably formed by crosslinking the surface layer of the tube.

There have been several descriptions in the literature of the method for crosslinking polymeric materials by ultraviolet rays, radiation and electrical discharge. U.S. Pat. No. 3,687,832 describes a method for crosslinking polymeric materials by electrical discharge at a pressure of at least 100 mm of mercury. Polymer Preprints, Japan, Vol. 26 (published by the Society of Polymer Science, Japan, Oct. 1st, 1977) describes a method of reducing the migration of dioctyl phthalate from the polyvinyl chloride sheet to blood by the treatment of cold plasma. The literature concerns the method of treating only sheets of polymeric materials and there are no descriptions of the method of treating the inner surface of plastic tubing because of the difficulty of treating the inside of the tube. PB Report PB 259,106 describes the method of treatment of aluminum foil placed in a glass tube by cold plasma, but there is not any description of the method of treating plastic tubing and the reduction of the migration and volatization of additives in the literature.

We have made this invention by the new method of treating the inner surface of a plastic tube by cold plasma which forms the crosslinked thin layer on the inner surface thereof substantially reducing the migration and volatilization of additives. It is therefore a principle object of the present invention to provide a plastic tube having the crosslinked thin layer at least on its inner surface, which substantially reduces the migration and volatilization of additives. There are some other alternative energy sources such as UV rays and radiation to produce the plastic tube of the present invention. But it is not efficient to use ultraviolet rays, particularly in treating the inner surface of a plastic tube, because a plastic tube is opaque to ultraviolet ray. High energy radiation is so powerful as to cause a serious problem in that it crosslinks the polymeric materials of a tube leaving it hard and brittle. It is therefore not preferable in producing the plastic tube of the present invention to use ultraviolet rays and high energy radiation.

The cold plasma described above, can effectively crosslink only a surface of a plastic tube without any change of its inherent properties as a plastic tube. The crosslinked thin layer on the inner surface of a tube properly formed by cold plasma reduces the diffusion, migration and volatilization of additives which are blended with polymeric materials of a tube. According to the preferred aspect of the invention, the polymeric material of a plastic tube is polyvinyl chloride, being either the polyvinyl chloride homopolymer or copolymers with other monomers, such as vinylidene chloride, or a polymer blended with other polymers such as polyvinyl acetate. The power requirement for these polymeric materials to form a crosslinked thin layer is lower than that for other polymeric materials. Moreover it is commercially more useful to increase the surface barrier properties of these polymeric materials than others, because they contain larger amounts of additives than other polymeric materials and these additives migrate and volatilize more easily than those for other polymers.

DETAILED DESCRIPTION OF THE INVENTION

Figure 1:
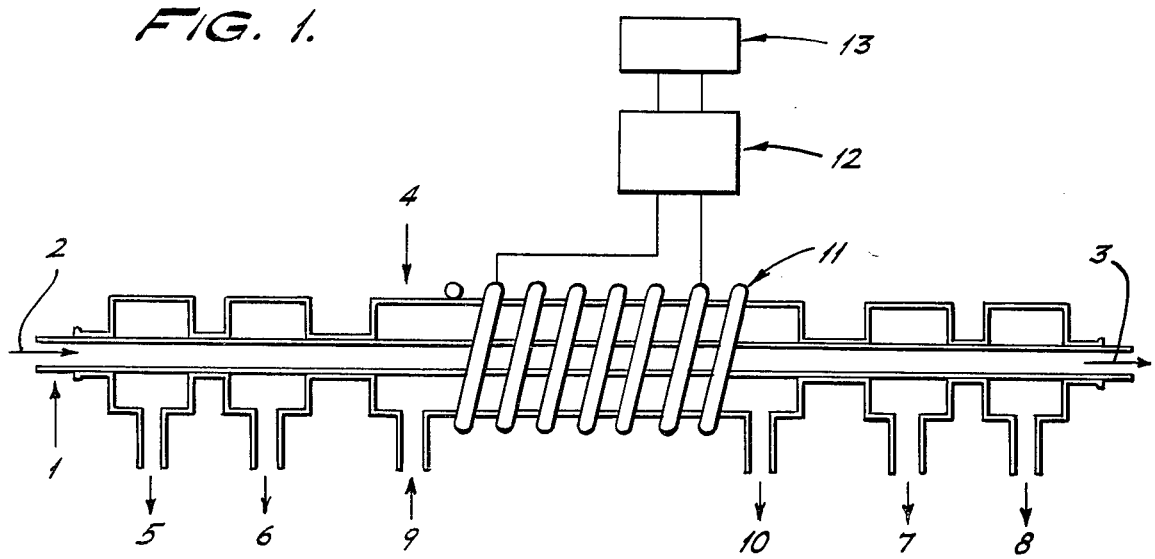
FIGS. 1 and 2 schematically represent two examples of an apparatus to produce the tube of the invention.
Figure 2:
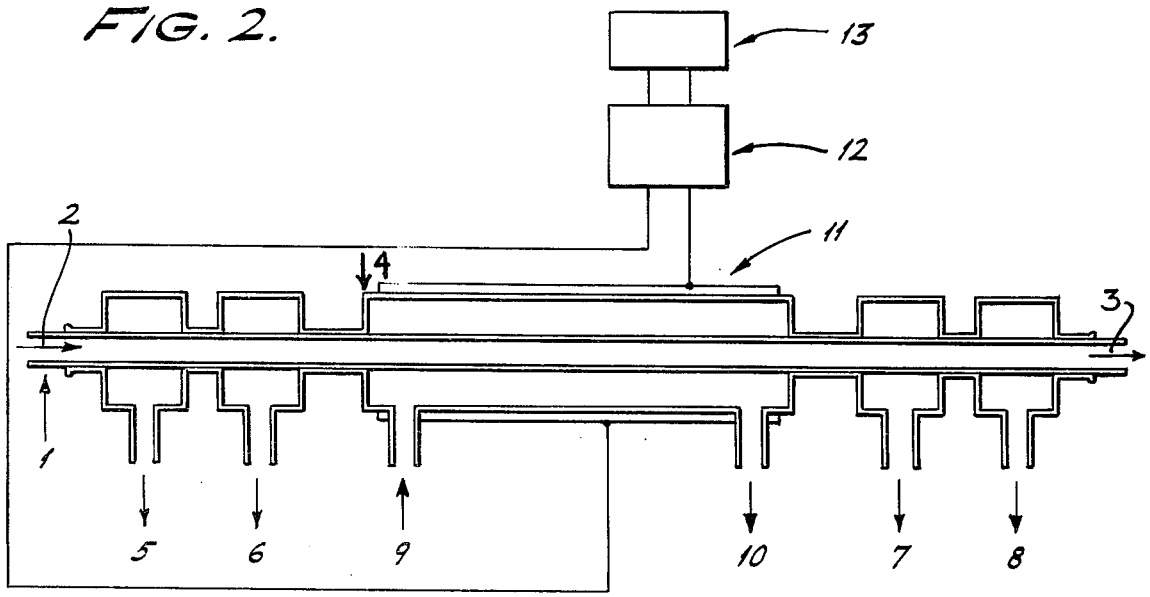

The present invention will become more apparent by the following detailed description of the properties of the tube and those of the treatment method. FIG. 1 is a longitudinal cross-sectional view of one typical type of the apparatus suitable for carrying out the present invention. FIG. 2 is another type of the apparatus suitable for carrying out the present invention. FIGS. 1 and 2 schematically represent two types of the apparatus for the treatment of the inner sides of a plastic tube by cold plasma. The inside pressure of a plastic tube 1 is controlled at a suitable pressure between 0.1 Torr and 5 Torr to initiate the electrical discharge by changing the flow rate of gases, such as argon, carbon monoxide and a mixture of gases, introduced from the right-hand side of tube 2 and the evacuation speed of the vacuum pump from exhaust pipe 3. The tube is moving continuously from the right-hand side to the left-hand side through a glass apparatus 4. Both ends of glass apparatus 4 almost touch with plastic tube 1 forming a tight seal so that air flowing into glass apparatus 4 is minimized. When glass apparatus 4 is evacuated through exhaust pipes 5, 6, 7, 8, the inside pressure of glass apparatus 4 is reduced. The pressure is regulated at between 0.5 Torr and 10 Torr, which is higher than that of a plastic tube, by the introduction of such gases as air, nitrogen, sulfur-hexafluoride and a mixture of gases through an inlet port 9 and the evacuating speed of the vacuum pump from exhaust pipe 10. The electrical power applied from a power supplier 13 is connected with electrode 11 through matching circuit 12. An electrical discharge is initiated and sustained only inside of plastic tube 1 at the center of the glass apparatus 4, while no discharge takes place inside of glass apparatus 4 because of pressure differences between two zones.

According to the present invention, for the treatment by cold plasma, two typical discharge electrodes 11, are shown in FIGS. 1 and 2. In a preferred aspect for the treatment of this invention, the frequency of applied power is higher than about 1 kilocycle per second, since it has been found that an electrical discharge is easily initiated by using a higher frequency power supply. During treatment the plasma temperature in the discharge rises; a plastic tube treated in cold plasma tends to be soft and eventually deforms and collapses. In the method of the present invention the pressure difference between the inside and outside of the plastic tube is small, so that the plastic tube is not likely to collapse due to the pressure differences.

By the procedure described hereinbefore, the crosslinked thin layer is formed on the inner surface of the tube and this thin layer is insoluble in solvents such as tetrahydrofuran which can dissolve the untreated polymeric materials of a tube. The barrier effect of said crosslinked thin layer is evaluated as follows. The treated tube is cut into 10 cm or so. One end is plugged close and the other is open. A specific amount of solvent is fed into this tube. Then the open end is plugged closed. After a few hours at a specific temperature, preferably around 40° C., the solvent in the tube is sampled and the contents of additives extracted from the polymeric materials of the tube is measured by gas-chromatography. In many cases the extracted plasticizer of a properly treated polyvinyl chloride tube can be reduced from one-tenth to several one hundredths of that of the untreated.

The structure of the crosslinked thin layer can be observed by an electron microscope after dying the tube with osmic acid and the thickness of the crosslinked thin layer can be measured by use of an electron microscopic photograph of the tube. It has been found that the growth rate of the crosslinked thin layer on the tube depends on plasma conditions such as plasma gas composition, gas pressure, flow rate of gas and the electrical power applied to an electrode. The thickness of the crosslinked thin layer increases in proportion to the treating time. The results shown in the table of example 2 indicate some of the interrelationships between the thickness of the crosslinked thin layer and the amount of migration of additives. When the thickness of the crosslinked thin layer is thinner than about 0.1 micron, the surface barrier properties are not so effective. Here it it understood that the crosslinked thin layer is not so highly crosslinked that additives can easily migrate in that layer. When the thickness of the crosslinked thin layer is thicker than about 1 micron, the amount of the migration of additives through the thin layer increases unexpectedly. Here it is understood that the crosslinked thin layer is so highly crosslinked that the swelling rate of the crosslinked thin layer with the solvent in the tube is extremely lower than that of the polymeric materials of the tube so that microcracks in the crosslinked thin layer are formed and additives can migrate through these microcracks. Consequently in the present invention it is most preferable that the thickness of the crosslinked thin layer of the polyvinyl chloride tube is about 0.1 to 1 micron in thickness. Usually the formation of the inner surface crosslinked thin layer is most effective as a barrier to the extraction by the fluid inside the tube. An outer surface crosslinked thin layer is, however, necessary for the sake of the reduction of additives volatilizing to atmosphere in the specific applications. It is a more favourable aspect of the present invention that the polyvinyl chloride tube of the invention be of tougher solvent resistance and higher surface tension. And what is more important for medical use of plastic tubes is that the inside of the tube be sterilized by the treatment of the cold plasma, so it is not necessary to remove undesirable microorganisms inside of the tube before using it.

The following are examples of the invention.

EXAMPLE 1

The apparatus shown in FIG. 1 was employed to produce the tube of the invention. A polyvinyl chloride tube ($3\phi \times 4.6\phi$) which is commercially available was placed in the apparatus. The inside pressure of the tube was regulated at 1 Torr with argon gas and the inside pressure of the glass apparatus was regulated at 20 Torr with air. Then the apparatus was electrically connected to an electrical power supplier delivering an alternating current of 13.56 megacycles per second to initiate electrical gas discharge. The electrical power applied to the apparatus was 50 W. The tube was treated by cold plasma generated inside of the tube by electrical gas discharge for 1 minute. After the tube was removed from the apparatus, a portion of the tube was cut open and then the surface tension of the inner surface of the tube was measured. The results are shown in the following Table I. A section cut from the tube was put into tetrahydrofuran and after a few minutes, the remaining insoluble thin layer was observed in the solvent. So it has been clearly concluded the the tube has a crosslinked thin layer. 5 ml of n-hexane was placed in the tube, both sides of which was squeezed in order not to leak the solvent, and the tube was warmed at 40° C. for 2 hours. Then the amount of the plasticizer, dioctylphthalate (abbreviated as DOP hereinafter), extracted from the solvent was measured by gas chromatography. The results are as shown in the following Table I.

TABLE I

| Sample | Surface tension (dyne/cm) | Amount of DOP in n-hexane (ppm mg/l) |
|---|---|---|
| Control tube | 36 | 17.990 |
| Tube of the present invention | 63 | 30 |

The tube of the invention, having a crosslinked thin layer on its inner surface shows the migration of DOP tube about one six hundredth as small as the control tube.

EXAMPLE 2

A surgical grade polyvinyl chloride tube (3/16"×5/16") which is commercially available under the trade name Tygon S-50-HL from Norton Plastic and Synthetics Division, U.S.A., was placed in the apparatus as shown in FIG. 2. The inside pressure of the tube was controlled at 1 Torr with carbon monoxide gas and the inside pressure of the glass apparatus was controlled at 5 Torr with air. Then high voltage was applied to the electrodes from the electrical power supplier delivering an alternating current of 110 kilocycles per second to initiate the electrical gas discharge. The electrical power applied to the apparatus was 300 W. The tube was treated by cold plasma generated inside for various discharge times. After the treatment, the thickness of the crosslinked layer of sections cut from each sample tube was measured with an electron microscope after dyeing said sections with osmic acid. The extracted plasticizers in 10 ml n-hexane were also measured, in the same way under the same conditions as described in example 1. The results are as shown in the following Table II.

TABLE II

| Sample | Thickness of crosslinked layer (micron) | Amount of DOP in n-hexane (ppm) |
| --- | --- | --- |
| Control tube | 0.00 | 98,582 |
| Tube treated by cold plasma | 0.02 | 65,721 |
| Tube treated by cold plasma | 0.05 | 5,572 |
| Tube treated by cold plasma | 0.07 | 2,754 |
| Tube treated by cold plasma | 0.10 | 939 |
| Tube treated by cold plasma | 0.45 | 493 |
| Tube treated by cold plasma | 0.70 | 445 |
| Tube treated by cold plasma | 1.00 | 548 |
| Tube treated by cold plasma | 1.50 | 1,232 |
| Tube treated by cold plasma | 2.00 | 3,791 |

When the thickness of the crosslinked thin layer is between 0.1 micron to 1 micron, the amount of extracted DOP is less than about one-hundredth of that of the control tube.

What is claimed is:

1. Polyvinyl chloride tube for carrying a fluid, said tube having a body portion composed of polyvinyl chloride mixed with a plasticizer or other additive which tends to migrate from said body portion to said fluid, said tube having a crosslinked thin layer on its inner surface, said layer having a critical thickness of about 0.1 to about 1 micron thereby substantially reducing the migration of said plasticizer or other additive from the body portion of said polymeric tube into the fluid located in said tube.

2. Polyvinyl chloride tube of the claim 1 in which said crosslinked thin layer is formed by treatment with cold plasma.

3. Polyvinyl chloride tube of claim 1 in which said plasticizers mainly consist of dioctyl phthalate or other phthalic acid esters.

4. Polyvinyl chloride tube having a body portion composed of polyvinyl chloride mixed with a plasticizer or other additive which tends to migrate from said body portion, said tube having a crosslinked thin layer on its inner surface, said thin layer being so highly crosslinked that when said layer is thicker than about 1 micron the amount of migration of said plasticizer or other additive increases unexpectedly due to formation of microcracks in said crosslinked thin layer, said layer having a critical thickness of about 0.1 to about 1 micron thereby avoiding substantial formation of said microcracks and thereby substantially reducing the migration of said plasticizers or other additives from the body portion of said polymeric tube into the fluids located in said tube.

* * * * *